United States Patent
Bara

(10) Patent No.: US 6,761,881 B2
(45) Date of Patent: Jul. 13, 2004

(54) TRANSPARENT OR TRANSLUCENT COSMETIC COMPOSITIONS COLORED BY PIGMENTS

(75) Inventor: Isabelle Bara, Paris (FR)

(73) Assignee: L'Oreal, Paris (FR)

( * ) Notice: Subject to any disclaimer, the term of this patent is extended or adjusted under 35 U.S.C. 154(b) by 74 days.

(21) Appl. No.: 10/203,382

(22) PCT Filed: Dec. 11, 2001

(86) PCT No.: PCT/FR01/03941

§ 371 (c)(1),
(2), (4) Date: Aug. 9, 2002

(87) PCT Pub. No.: WO02/47606

PCT Pub. Date: Jun. 20, 2002

(65) Prior Publication Data

US 2003/0012752 A1 Jan. 16, 2003

(51) Int. Cl.⁷ ............................. A61K 7/025; A61K 7/48
(52) U.S. Cl. ............................. 424/63; 424/64; 424/401
(58) Field of Search ............................. 424/64, 63, 401; 514/944

(56) References Cited

U.S. PATENT DOCUMENTS 3,148,125 A  9/1964  Strianse et al. ................ 167/85

FOREIGN PATENT DOCUMENTS

| DE | 197 07 309 | 8/1998 |
| EP | 0 879 592 | 11/1998 |
| FR | 2 804 014 | 7/2001 |

*Primary Examiner*—Jyothsna Venkat
(74) *Attorney, Agent, or Firm*—Steptoe & Johnson LLP; D. Douglas Price

(57) ABSTRACT

The invention relates to colored transparent or translucent cosmetic compositions exhibiting a turbidity of less than 800 NTU and comprising, in a transparent or translucent cosmetic base, an amount of less than 0.5% by weight, with respect to the final cosmetic composition, of at least one colored pigment which is insoluble in the cosmetic base and which has a mean particle size of greater than 100 nm.

19 Claims, No Drawings

TRANSPARENT OR TRANSLUCENT COSMETIC COMPOSITIONS COLORED BY PIGMENTS

The present invention relates to transparent or translucent cosmetic compositions colored by pigments.

Transparent or translucent cosmetic compositions are usually colored by dyes which are soluble in the cosmetic support and which exhibit the advantage of not scattering light and of thus retaining the properties of transparency of the compositions comprising them. U.S. Pat. No. 3,148,125 discloses transparent lipsticks colored by dyes.

However, the number of dyes, and in particular of fat-soluble dyes, which are authorized for use in cosmetics by various national laws is very limited. The range of colors which it may be hoped to obtain for compositions, in particular anhydrous lipophilic compositions, intended to be applied to all parts of the face or body is for this reason strictly limited.

Another approach for coloring transparent cosmetic compositions has been the use of pigments having sizes markedly lower than the wavelengths of visible light, that is to say lower than 200 nm (i.e., the lowest wavelength of the visible spectrum 400 nm divided by 2), or better still lower than 100 nm. JP 0 220 7014 and EP 79 612 disclose transparent cosmetic compositions comprising pigments with a very small size ranging up to 300 Å. These nanopigments, among which may be mentioned brown and black iron oxides and white titanium dioxides, are, however, also very limited in number and do not make possible the production of a broad range of colors.

Furthermore, the use of these pigments requires very thorough milling and the stability of the compositions over time often proves to be unsatisfactory.

There consequently still exists a need for a method for coloring transparent or translucent cosmetic compositions by physiologically acceptable coloring agents which makes it possible to obtain a wide range of colors while maintaining the transparency of the support.

The inventor has discovered, surprisingly, that it is possible to obtain colored translucent or transparent cosmetic compositions by incorporating, in transparent or translucent cosmetic supports, a very small fraction of pigments having sizes greater than those of the nanopigments used in the art.

A subject matter of the present invention is consequently colored transparent or translucent cosmetic compositions exhibiting a turbidity of less than 800 NTU and comprising, in a transparent or translucent cosmetic base, an amount of less than 0.03% by weight, with respect to the final cosmetic composition, of at least one colored pigment, insoluble in the cosmetic base, having a mean particle size of greater than 100 nm.

The colored pigments which can be used according to the present invention for the coloring of transparent or translucent compositions are chosen from the very great variety of colored inorganic, organic or composite pigments commonly used in the cosmetics field.

Mention may be made, by way of examples of inorganic pigments, of iron oxides, chromium oxide, chromium hydrate, ultramarines (polysulfides of aluminum silicates), cobalt blue, Prussian blue (ferric ferrocyanide), manganese violet, manganese pyrophosphate and some metal powders, such as silver or aluminum powders.

The organic pigments are chosen, for example, from carbon black, thioindigo or flaming red.

The composite pigments which can be used according to the present invention encompass in particular lakes, that is to say salts formed from certain metals (calcium, barium, aluminum, strontium, zirconium and their mixtures) and from organic acid dyes immobilized on an organic support, such as rosin, or on an inorganic support, such as alumina, barium sulfate, calcium carbonate, talc, clay, zinc oxide, titanium dioxide and combinations of these. Mention may be made, as examples of such lakes, of the calcium salt of lithol red B on rosin and barium sulfate (D&C Red No. 7 calcium lake) the aluminum salt of tartrazine on alumina (FD&C Yellow No. 5 aluminum lake), the aluminum salt of eosin on alumina and titanium dioxide (D&C Red No. 21 aluminum lake), the aluminum salt of phloxin B on alumina (D&C Red No. 27 aluminum lake), the aluminum salt of brilliant yellow FCF on alumina (FD&C Yellow No. 6 aluminum lake) and the aluminum salt of brilliant blue on alumina (FD&C Blue No. 1 aluminum lake).

If necessary, the colored pigments described above can be coated with various materials chosen, for example, from silicones, amino acids or fluorinated compounds. Such a coating may be useful, indeed even necessary, for improving the compatibility of the pigments with some cosmetic bases and stabilizing the dispersions obtained over time.

This great variety of pigments which can be used, alone or in combination, for the coloring of transparent or translucent compositions makes it possible to obtain an infinity of hues and thus makes it possible, particularly in the case of anhydrous lipophilic cosmetic bases, to overcome the disadvantage of the restricted range of colors available for compositions comprising dyes soluble in the base.

Another advantage of the transparent or translucent cosmetic compositions of the present invention is related to the size of the particles of the colored pigment or pigments used.

This is because the mean particle size of the pigments used according to the present invention is greater than 100 nm, and preferably greater than 200 nm.

The colored pigments used consequently do not exhibit the problems of instability of the dispersed state of the cosmetic compositions of the prior art comprising nanopigments having a size of less than 100 nm.

The pigments thus dispersed do not require such a thorough, and therefore such a lengthy and expensive, milling as pigments with a size of less than 100 nm.

The transparent or translucent dispersions colored by the pigments indicated above having a mean size of greater than 100 nm exhibit a satisfactory long-term stability and only require small amounts of dispersing agent, indeed even no dispersing agent at all.

The amount of pigments used in the colored transparent or translucent cosmetic compositions of the present invention depends on certain parameters, such as the nature, the mean size and the coloring power of the pigment particles, the hue, the transparency and the color intensity which are desired, or the chemical nature of the cosmetic base used. It is generally a matter of finding the best compromise between minimum turbidity and maximum color intensity.

Generally, the concentration of the colored pigment or pigments in the transparent or translucent cosmetic compositions of the present invention is less than 0.03% by weight, and preferably less than 0.0 1% by weight, with respect to the final cosmetic composition.

In one embodiment of the present invention, the transparent or translucent cosmetic compositions comprise at most 0.001% by weight of colored pigment.

The term "transparent or translucent compositions" according to the present invention is understood to mean compositions exhibiting a turbidity, measured according to the method described below, of less than 800 NTU (Nephelometric Turbidity Units) and preferably less than 500 NTU.

The turbidity is measured using a model 2100 P turbidimeter from Hach at ambient temperature (20 to 25° C.). The tubes used for the measurement are referenced AR 397 A cat 24347-06. The device is calibrated using formazine suspensions with different concentrations.

Use may be made, as transparent or translucent cosmetic base for the preparation of the colored transparent or translucent cosmetic compositions of the present invention, of any known cosmetic base, provided that it satisfies the transparency requirements indicated above. This is because it is obvious that the cosmetic base used, devoid of colored pigments, must exhibit a transparency or translucency which is sufficient for the value of the turbidity of the final composition colored by pigments not to exceed the limit values indicated above.

The transparent or translucent cosmetic base can be a hydrophilic or lipophilic phase with a liquid, thickened, gelled, pasty or solid consistency. It can, for example, be a water-in-oil emulsion, an oil-in-water emulsion, a hydrophilic or lipophilic solid gel, a soft gel or an oily lotion.

Preferably, the base of the composition is in the form of an aqueous or oily gel which is more or less rigid. More specifically, this gel is a rigid gel presented in a dish or as a stick, preferably as a stick, and in the anhydrous form.

The lipophilic base can be a fatty phase which is liquid at ambient temperature, such as those used conventionally in cosmetics. This fatty phase can comprise polar oils and/or nonpolar oils.

In particular, the polar oils of the invention are:

(1) hydrocarbonaceous vegetable oils with a high content of triglycerides composed of esters of fatty acids and of glycerol, the fatty acids of which can have various $C_4$ to $C_{24}$ chain lengths, it being possible for the chains to be linear or branched and saturated or unsaturated; these oils are in particular wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, lye, safflower, candlenut, passionflower or musk rose oil; or triglycerides of caprylic/capric acids, such as those sold by Stearineries Dubois or those sold under the names Miglyol 810, 812 and 818 by Dynamit Nobel;

(2) synthetic oils or synthetic esters of formula $R_aCOOR_b$ in which $R_a$ represents the residue of a linear or branched fatty acid comprising from 1 to 40 carbon atoms and $R_b$ represents a hydrocarbonaceous chain, in particular a branched hydrocarbonaceous chain, comprising from 1 to 40 carbon atoms, provided that $R_a+R_b$ is $\geq 10$, such as, for example, purcellin oil (cetearyl octanoate), isononyl isononanoate, $C_{12}$ to $C_{15}$ alkyl benzoate, isopropyl myristate, 2-ethyihexyl palmitate, isostearyl isostearate, or octanoates, decanoates or ricinoleates of alcohols or of polyalcohols; hydroxylated esters, such as isostearyl lactate or diisostearyl malate; and pentaerythritol esters;

(3) synthetic ethers having from 10 to 40 carbon atoms;

(4) $C_8$ to $C_{26}$ fatty alcohols, such as oleyl alcohol;

(5) $C_8$ to $C_{26}$ fatty acids, such as oleic acid, linolenic acid and linoleic acid; and (6) mixtures thereof.

The nonpolar oils according to the invention are in particular silicone oils, such as volatile or nonvolatile and linear or cyclic polydimethylsiloxanes (PDMS) which are liquid at ambient temperature; polydimethylsiloxanes comprising side alkyl or alkoxy groups and/or alkyl or alkoxy groups at the chain end, which groups each have from 2 to 24 carbon atoms; phenylated silicones, such as phenyl trimethicones, phenyl dimethicones, phenyltrimethylsiloxydiphenyl-siloxanes, diphenyl dimethicones, diphenylmethyl-diphenyltrisiloxanes or (2-phenylethyl)trimethyl-siloxysilicates; linear or branched and volatile or nonvolatile hydrocarbons of synthetic or mineral origin, such as volatile liquid paraffins (isoparaffins, such as isododecane) or nonvolatile liquid paraffins, and their derivatives, liquid petrolatum, liquid lanolin, polydecenes, hydrogenated polyisobutene, such as parleam oil, squalane or arara oil; and their mixtures.

Preferably, the oils are nonpolar oils and more especially an oil or a mixture of oils of the hydrocarbonaceous type of mineral or synthetic origin chosen in particular from alkanes, such as parleam oil, isoparaffins, such as isododecane, squalane and their mixtures. These oils are advantageously used in combination with one or more phenylated silicone oils.

The liquid fatty phase preferably comprises at least one nonvolatile oil chosen in particular from hydrocarbonaceous oils of mineral, vegetable or synthetic origin, synthetic esters or ethers, silicone oils and their mixtures.

The total liquid fatty phase represents, in practice, from 5 to 99.95%, preferably from 10 to 80%, and more preferably from 20 to 75%, of the total weight of the composition.

This fatty phase is advantageously structured by a gelling agent for fatty phases, such as:

(1) gelling polyamides, in particular with a molecular mass of less than 100 000, and preferably of less than 50 000, for example with a molecular mass ranging from 2 000) to 20 000, optionally comprising side alkyl groups or alkyl groups at the chain end having from 8 to 120 carbon atoms, and preferably from 12 to 60 carbon atoms, (2) hydrophobic galactomannans comprising in particular from 1 to 6, and preferably from 2 to 4, OH groups per monosaccharide unit which are substituted by a $C_{1-6}$, preferably $C_{1-3}$, alkyl group, (3) hydrophobic pyragenic silicas, (4) and the combinations of these gelling agents.

The gelling polyamides are, for example, the polyamide resins resulting from the condensation of an aliphatic dicarboxylic acid and of a diamine, including the compounds having more than 2 carboxyl groups and more than 2 amine groups, the carboxyl arid amine groups of adjacent individual units being condensed via an amide bond. These polyamide resins are in particular those sold under the Versamid® trademark by General Mills Inc. and Henkel Corp. (Versamid® 930, 744 or 1655) or by Olin Mathieson Chemical Corp. under the Onamnid® trademark, in particular Onamid® S or C. These resins have a weight-average molecular mass ranging from 6 000 to 9 000. For further information on these polyamides, reference may be made to U.S. Pat. Nos. 3,645,705 and 3,148,125. More especially, Versamid® 930 or 744 is used.

Use may also be made of the polyamides sold by Arizona Chemical under the Uni-Rez references (2658, 2931, 2970, 2621, 2613, 2624, 2665, 1554, 2623, 2662) and the product sold under the reference Macromelt 6212 by Henkel. For further information on these polyamides, reference may be made to U.S. Pat. No. 5,500,209.

The polyamides can also be those resulting from a polycondensation between a carboxylic diacid comprising at least 32 carbon atoms (in particular from 32 to 44 carbon atoms) and a diamine having at least 2 carbon atoms (in particular from 2 to 36 carbon atoms). The diacid is preferably a dimer of a fatty acid having at least 16 carbon atoms, such as oleic, linoleic or linolenic acid. The diamine is preferably ethylenediamine, hexylenediamine or hexamethylenediamine. If the polymers comprise one or two end carboxylic acid groups, it is advantageous to esterify them with a monoalcohol having at least 4 carbon atoms, preferably from 10 to 36 carbon atoms, more preferably from 12 to 24 carbon atoms, and still more preferably from 16 to 24 carbon atoms, for example, 18 carbon atoms.

These polymers are more especially those disclosed in U.S. Pat. No. 5,783,657 of Union Camp. Each of these polymers satisfies in particular the following formula (I):

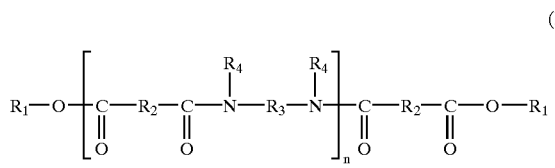

(I)

in which n denotes a whole number of amide units such that the number of ester groups represents from 10% to 50% of the total number of the ester and amide groups; each of the $R_1$ symbols independently denotes an alkyl or alkenyl group having at least 4 carbon atoms and in particular from 4 to 24 carbon atoms; each of the $R_2$ symbols independently represents a $C_4$ to $C_{42}$ hydrocarbonaceous group, provided that 50% of the $R_2$ groups represent a $C_{30}$ to $C_{42}$ hydrocarbonaceous group; each of the $R_3$ symbols independently represents an organic group provided with at least 2 carbon atoms, with hydrogen atoms and optionally with one or more oxygen or nitrogen atoms; and each of the $R_4$ symbols independently represents a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$-N-$R_3$, with at least 50% of the $R_4$ groups representing a hydrogen atom.

In the specific case of the formula (I), the optionally functionalized end fatty chains within the meaning of the invention are end chains bonded to the final heteroatom, in this instance nitrogen, of the polyamide backbone.

In particular, the ester groups of the formula (I), which form part of the end and/or side fatty chains within the meaning of the invention, represent from 15 to 40% of the total number of the ester and amide groups, and more preferably from 20 to 35%. Furthermore, n advantageously represents an integer ranging from 1 to 5, and preferably of greater than 2.

Preferably, $R_1$ is a $C_{12}$ to $C_{22}$ alkyl group and more preferably a $C_{16}$ to $C_{22}$ alkyl group. Advantageously, $R_2$ can be a $C_{10}$ to $C_{42}$ hydrocarbonaceous (alkylene) group. Preferably, at least 50%, and more preferably at least 75%, of the $R_2$ symbols are groups having from 30 to 42 carbon atoms. The other $R_2$ symbols are $C_4$ to $C_{19}$ and even $C_4$ to $C_{12}$ hydrogenated groups. Preferably, $R_3$ represents a $C_2$ to $C_{36}$ hydrocarbonaceous group or a polyoxyalkylene group and $R_4$ represents a hydrogen atom. More preferably, $R_3$ represents a $C_2$ to $C_{12}$ hydrocarbonaceous group.

The hydrocarbonaceous groups can be linear, cyclic or branched and saturated or unsaturated groups. Furthermore, the alkyl and alkylene groups can be linear or branched and saturated or unsaturated groups.

According to the invention, the structuring of the liquid fatty phase is preferably obtained using one or more polymers of formula (I). The polymers of formula (I) are generally provided in the form of blends of polymers, it being possible for these blends to additionally comprise a synthetic product corresponding to a compound of formula (I) where n has the value 0, that is to say a diester.

These polymers, because of their fatty chain(s), exhibit good solubility in oils and thus result in macroscopically homogeneous compositions, even with a high level (at least 25%) of polymer, in contrast to polymers devoid of a fatty chain.

Mention may be made, as preferred structuring polymers of formula (I) which can be used in the invention, of polyamides modified by side fatty chains and/or end fatty chains having from 8 to 120 carbon atoms, and in particular from 12 to 68 carbon atoms, the end fatty chains being bonded to the polyamide backbone via ester groups. These polymers preferably comprise a fatty chain at each end of the polymer backbone and in particular of the polyamide backbone.

Mention may be made, as examples of structuring polyamides of formula (I) which can be used in the composition according to the invention, of the commercial products sold by Arizona Chemical under the names Uniclear® 80 and Uniclear® 100. They are sold respectively in the form of an 80% (as active material) gel in a mineral oil and of a 100% (as active material) gel. They have a softening point of 88 to 94° C. These commercial products are a blend of copolymers of a $C_{36}$ diacid condensed with ethylenediamine, with a weight-average molecular mass respectively of approximately 600 or 4 000. The end ester groups result from the esterification of the remaining acid endings with cetyl alcohol or stearyl alcohol or their mixtures (also known as cetearyl alcohol).

The galactomannans are in particular ethylated guar derivatives having especially a degree of substitution of 2 to 3, such as those sold by Aqualon under the names N-Hance-AG-200® or N-Hance-AG-50®.

The pyrogenic silica preferably exhibits a particle size which can be nanometric to micrometric, for example ranging from approximately from 5 to 200 nm.

Pyrogenic silicas can be obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces. Such hydrophilic silicas are sold, for example, under the names Aerosil 130®, Aerosil 200®, Aerosil 255®, Aerosil 300® or Aerosil 380® by Degussa or under the names Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica by a chemical reaction which reduces the number of silanol groups. It is possible in particular to substitute silanol groups by hydrophobic groups and thus to obtain a hydrophobic silica. The hydrophobic groups can be:

(1) trimethylsiloxy groups, which are obtained in particular by treatment of pyrogenic silica in the presence of hexamethyldisilazane and are named "Silica silylate" according to the CTFA (6th edition, 1995); they are sold, for example, under the name Aerosil R812® by Degussa and under the name Cab-O-Sil TS-530® by Cabot;

(2) dimethylsilyloxy or polydimethylsiloxane groups, which are obtained in particular by treatment of pyrogenic silica in the presence of polydimethylsiloxane or of dimethyldichiorosilane and are named "Silica dimethyl silylate" according to the CTFA (6th edition, 1995); they are sold, for example, under the names Aerosil R972® and Aerosil R974® by Degussa and under the names Cab-O-Sil TS-610® and Cab-O-Sil TS-720® by Cabot; and (3) groups resulting from the reaction of pyrogenic silica with alkoxysilanes or siloxanes; these treated silicas are, for example, those sold under the reference Aerosil R805® by Degussa.

To produce an aqueous gel, use may be made of any gelling agent for aqueous phases of the cellulose derivative type, such as hydroxyethylcellulose and carboxymethylcellulose, or acrylic derivative type, such as crosslinked copolymers of acrylic acid and of $C_{10-30}$ alkyl acrylates, for example the Pemulen® series and Carbopol® 980, sold by Goodrich, clay derivatives of the sodium magnesium silicate type, such as Laponite XLS or XLG, sold by Laporte, and the combinations of these gelling agents. The aqueous gel can be a water-based gel or a gel based on a water/alcohol mixture.

The gelling agent represents from 0.05 to 90% by weight, preferably from 2 to 60% by weight, and more preferably from 5 to 40% by weight, of the total weight of the colored cosmetic composition.

As explained above, the choice of a low fraction (less than 0.03% by weight) of colored pigments which are insoluble in the cosmetic base and which have the specific sizes indicated above is reflected by particularly attractive advantages in the case of an anhydrous lipophilic base, that is to say of a base which does not make possible the dissolution of hydrophilic soluble dyes.

In a preferred embodiment of the invention, the cosmetic base is consequently an anhydrous lipophilic base.

The colored transparent or translucent cosmetic compositions according to the present invention can comprise, in addition to the colored pigments described above, one or more white pigments, such as titanium dioxide, zirconium dioxide, cerium dioxide or zinc oxide.

The colored transparent or translucent cosmetic compositions according to the present invention can additionally comprise additives commonly used in the cosmetics field, such as, for example, dispersing agents, fragrances, sunscreen agents, preservatives, antioxidants or cosmetic active principles, provided, of course, that the addition of these optional constituents does not detrimentally affect the transparency or translucency properties inherent to the cosmetic compositions of the present invention.

The present invention is illustrated by the following examples:

EXAMPLE 1

A colored transparent lip balm is prepared from the following ingredients:

| | |
|---|---|
| Uniclear ® 100* | 25% |
| Octyldodecanol | 10% |
| Iron oxides | 0.0006% |
| Solsperse ® 21000** | 0.00002% |
| Fragrance | 4% |
| Parleam oil | q.s. for 100% by weight |

*condensate of a hydrogenated $C_{36}$ diacid and of ethylenediamine esterified with stearyl alcohol (molar mass approximately 4 000), sold by Arizona Chemical.
**dispersing agent sold by Avecia Pigments and Additifs A dispersion of the pigments in the parleam oil is prepared in the presence of the dispersing agent. This dispersion is incorporated in the other ingredients (Uniclear® 100 and octyldodecanol) heated to 100° C. while maintaining the mixture under slow stirring over 30 minutes. After casting in molds and cooling to ambient temperatures a solid composition with a pinkish beige color exhibiting a turbidity of 87.3 NTU is obtained.

EXAMPLE 2

A colored transparent anhydrous scenting gel for the body is prepared by mixing the following ingredients:

| | |
|---|---|
| Silicone resin of KSG 6* type | 43% |
| Pentacyclodimethicone | 43% |
| Aluminum lake of brilliant blue FCF on alumina (12/88) (Blue 1 lake) | 0.001% |
| Solsperse 21000** | 0.000025% |
| Fragrance | 4% |
| Parleam oil | q.s. for 100% by weight |

*sold by Shin Etsu
**dispersing agent sold by Avecia Pigments and Additifs

The gel obtained is blue in color and exhibits a turbidity of 39.6 NTU.

What is claimed is:

1. A transparent or translucent colored cosmetic composition having a turbidity of less than 800 NTU and comprising, in a transparent or translucent cosmetic base, an amount of less than 0.03% by weight, with respect to the total weight of the cosmetic composition, of at least one colored pigment which is insoluble in the cosmetic base and which has a mean particle size of greater than 100 nm.

2. The colored cosmetic composition as claimed in claim 1, wherein the colored pigment has a mean particle size of greater than 200 nm.

3. The colored cosmetic composition as claimed in claim 1, wherein the concentration of the colored pigment is less than 0.01% by weight with respect to the total weight of the cosmetic composition.

4. The colored cosmetic composition as claimed in claim 3, wherein the concentration of the colored pigment is at most equal to 0.001% by weight with respect to the total weight of the cosmetic composition.

5. The colored cosmetic composition as claimed in claim 1, wherein the composition has a turbidity of less than 500 NTU.

6. The colored cosmetic composition as claimed in claim 1, wherein the colored pigment is an organic, inorganic or composite pigment.

7. The colored cosmetic composition as claimed in claim 6, wherein the inorganic pigment is iron oxide, chromium oxide, chromium hydrate, ultramarine, cobalt blue, Prussian blue, manganese violet, manganese pyrophosphate or a metal powder.

8. The colored cosmetic composition as claimed in claim 6, wherein the organic pigment is carbon black, thioindigo or flaming red.

9. The colored cosmetic composition as claimed in claim 6, wherein the composite pigment is a lake or salt formed from calcium, barium, aluminum, strontium, zirconium or their mixtures or from an organic acid dye immobilized on an organic or inorganic support.

10. The colored cosmetic composition as claimed in claim 9, wherein the lake is a calcium salt of lithol red B on rosin and barium sulfate, an aluminum salt of tartrazine on alumina, an aluminum salt of eosin on alumina and titanium dioxide, an aluminum salt of phloxin B on alumina, an aluminum salt of brilliant yellow FCF on alumina or an aluminum salt of brilliant blue on alumina.

11. The colored cosmetic composition as claimed in claim 1, wherein the colored pigment is coated with a silicone, an amino acid or a fluorinated compound.

12. The colored cosmetic composition as claimed in claim 1, wherein the composition additionally comprises at least one white pigment which is titanium dioxide, zirconium dioxide, cerium dioxide or zinc oxide.

13. The colored cosmetic composition as claimed in claim 1, wherein the cosmetic base is an aqueous or oily gel.

14. The colored cosmetic composition as claimed in claim 13, wherein the gel is in a form of a stick.

15. The colored cosmetic composition as claimed in claim 1, wherein the cosmetic base is an anhydrous lipophilic cosmetic base.

16. The colored cosmetic composition as claimed in claim 1, wherein the cosmetic base is an anhydrous gel formed of a fatty phase which is liquid at ambient temperature comprising a polar and/or nonpolar oil, which fatty phase is structured by a gelling agent for a fatty phase which is an hydrophobic pyrogenic silica, a gelling polyamide, hydrophobic galactomannan, or mixture thereof.

17. The colored cosmetic composition as claimed in claim 16, wherein the gelling polyamide corresponds to the formula (I):

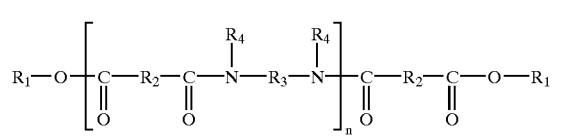

(I)

in which n denotes a whole number of amide units such that the number of ester groups represents from 10% to 50% of the total number of the ester and amide groups; each $R_1$ independently denotes an alkyl or alkenyl group having at least 4 carbon atoms; each $R_2$ independently represents a $C_4$ to $C_{42}$ hydrocarbonaceous group, provided that 50% of the $R_2$ groups represent a $C_{30}$ to $C_{42}$ hydrocarbonaceous group; $R_3$ independently represents an organic group provided with at least 2 carbon atoms, with hydrogen atoms and optionally with one or more oxygen or nitrogen atoms; and each $R_4$ independently represents a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$-N-$R_3$, with at least 50% of the $R_4$ groups representing a hydrogen atom.

18. The cosmetic composition of claim 17, wherein each $R_1$ independently denotes an alkyl or alkenyl group having 4 to 24 carbon atoms.

19. The cosmetic composition as claimed in claim 1, wherein the composition additionally comprises a physiologically acceptable additive which is a dispersing agent, a fragrance, a sunscreen agent, a preservative, an antioxidant or a cosmetic active principle.

* * * * *